United States Patent
Hadlock et al.

[11] Patent Number: 5,925,053
[45] Date of Patent: Jul. 20, 1999

[54] MULTI-LUMEN POLYMERIC GUIDANCE CHANNEL, METHOD FOR PROMOTING NERVE REGENERATION, AND METHOD OF MANUFACTURING A MULTI-LUMEN NERVE GUIDANCE CHANNEL

[75] Inventors: Theresa Anne Hadlock, Arlington; Cathryn Sundback, Harvard, both of Mass.

[73] Assignee: Children's Medical Center Corporation, Boston, Mass.

[21] Appl. No.: 08/921,908

[22] Filed: Sep. 2, 1997

[51] Int. Cl.[6] ............................................. A61B 17/08
[52] U.S. Cl. ..................... 606/152; 606/152; 606/154; 606/155
[58] Field of Search ....................... 606/152, 153, 606/154, 155, 156; 623/1, 11, 12

[56] References Cited

U.S. PATENT DOCUMENTS

| | | | |
|---|---|---|---|
| 4,759,764 | 7/1988 | Fawcett et al. | 623/12 |
| 4,778,467 | 10/1988 | Stensaas et al. | 623/12 |
| 4,806,621 | 2/1989 | Kohn et al. | 528/211 |
| 4,878,913 | 11/1989 | Aebischer et al. | 623/12 |
| 5,011,486 | 4/1991 | Aebischer et al. | 606/152 |
| 5,024,671 | 6/1991 | Tu et al. | 623/1 |
| 5,026,381 | 6/1991 | Li | 606/152 |
| 5,030,225 | 7/1991 | Aebischer et al. | 606/152 |
| 5,047,181 | 9/1991 | Occhionero et al. | 264/28 |
| 5,092,871 | 3/1992 | Aebischer et al. | 606/152 |
| 5,202,120 | 4/1993 | Silver et al. | 424/93 |
| 5,358,475 | 10/1994 | Mares et al. | 623/66 |
| 5,370,681 | 12/1994 | Herweck et al. | 623/1 |
| 5,399,665 | 3/1995 | Barrera et al. | 528/354 |
| 5,654,381 | 8/1997 | Hrkach et al. | 525/450 |

*Primary Examiner*—Michael Buiz
*Assistant Examiner*—Vy Q. Bui
*Attorney, Agent, or Firm*—Thomas J. Engellenner; Nutter, McClennen & Fish, LLP

[57] ABSTRACT

A guidance channel or conduit for promoting nerve regeneration includes a body constructed of a biocompatible polymeric material and having a first end for connection to a proximal stump of a severed nerve and a second end for connection to a distal stump of the severed nerve. The body includes a plurality of internal lumens extending between the first and second end to facilitate rejoining of the proximal and distal stumps of the severed nerve by providing increased surface area for Schwann cell adherence. A method for promoting nerve regeneration using a multi-lumen nerve guidance channel is also disclosed.

14 Claims, 3 Drawing Sheets

MULTI-LUMEN POLYMERIC GUIDANCE CHANNEL, METHOD FOR PROMOTING NERVE REGENERATION, AND METHOD OF MANUFACTURING A MULTI-LUMEN NERVE GUIDANCE CHANNEL

BACKGROUND OF THE INVENTION

The present invention relates generally to repairing injured nerves. More particularly, the invention relates to a guidance channel or conduit, as well as a method, for promoting nerve regeneration.

Various prostheses and nerve grafts have been proposed for repairing severed nerves. Typical prostheses include synthetic tubular bodies having a single lumen through which nerve regeneration is intended to occur. These nerve guidance devices are surgically inserted into the gap between the proximal and distal nerve stumps in an effort to promote nerve growth.

Conventional nerve guidance channels are often unsuccessful. When a nerve is injured, Schwann cells stimulate the growth of the regenerating nerve fibers by dividing and producing the trophic substances responsible for nerve growth. Accordingly, Schwann cells appear to play an important role in the regeneration of nerve tissue in an injured or severed nerve. Conventional nerve prostheses and grafts may fail because they fail to support a sufficient number of Schwann cells to ensure successful nerve regeneration.

Accordingly, there is a need for an improved nerve prosthesis for promoting increased and reliable nerve regeneration between the distal and proximal stumps of a severed nerve.

It is, therefore, an object of the present invention to provide an effective nerve guidance channel for promoting nerve regeneration.

It is another object of the present invention to provide a nerve guidance channel which provides increased surface area for Schwann cell adherence.

It is also an object of the present invention to provide a more flexible and preferably biodegradable prosthesis that does not cause discomfort or require surgical removal.

It is a further object of the present invention to provide a nerve guidance channel or conduit that permits increased control over the direction of growth of regenerating nerve fibers.

SUMMARY OF THE INVENTION

The present invention is directed to a guidance channel or conduit and a method for promoting nerve regeneration. The guidance channel includes a body constructed of a biocompatible polymeric material and having a first end for connection to a proximal stump of a severed nerve and a second end for connection to a distal stump of the severed nerve. The body includes a plurality of internal lumens extending between the first and second end to facilitate rejoining of the proximal and distal stumps of the severed nerve by providing increased surface area for Schwann cell adherence.

In a preferred embodiment, the guidance channel is constructed of a bioresorbable or biodegradable material, such as poly-L-lactic acids, poly-lactic-coglycolic acid polymers, and polycaprolactones. The guidance channel can include between 5 and 5000 lumens. The inner diameter of each lumen is can be between approximately 2 and 500 microns.

In accordance with a further aspect of the present invention, Schwann cells are incorporated within the lumens of the nerve guidance channel body. The Schwann cells can adhere to the interior surfaces of the lumens.

In accordance with another aspect of the present invention, the body of the nerve guidance channel is constructed of a porous membrane structure which contains a plurality of pores for permitting fluids and nutrients to pass through the body of the guidance channel to reach the internal lumens. In this manner, Schwann cells and regenerative nerve tissue within the internal lumens are able to receive nutrients and oxygen during nerve regeneration. It is preferable for the pores to be sized to inhibit the growth of regenerative nerve tissue through the pores.

The method of the present invention provides for promoting nerve regeneration between the severed stumps of a nerve. The method includes the steps of providing a guidance channel constructed of a polymeric material and having a plurality of internal lumens extending between the first end and the second end of the guidance channel, connecting the proximal stump of the nerve to the first end of the guidance channel, and connecting the distal stump of the nerve to the second end of the guidance channel such that nerve regeneration occurs within the plurality of lumens of the guidance channel between the severed stumps of the nerves.

In accordance with a further aspect of the present invention, the method includes the step of lining the lumens of the plurality of lumens with Schwann cells.

A method of manufacturing a multi-lumen nerve guidance channel in accordance with present invention includes the steps of preparing a polymer solution comprising a polymer and a solvent, injecting the polymer solution into a mold to form the body of the nerve guidance channel, the mold including a plurality of wires for forming a plurality of internal lumens within the body, solidifying the polymer solution by freezing the body, and drying the body by sublimation to form a plurality pores within the body.

In accordance with another aspect of the present invention, the manufacturing method includes the step of adjusting the concentration of the solvent within the polymer solution to control the size and number of pores formed within the body.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION

Figure 1:
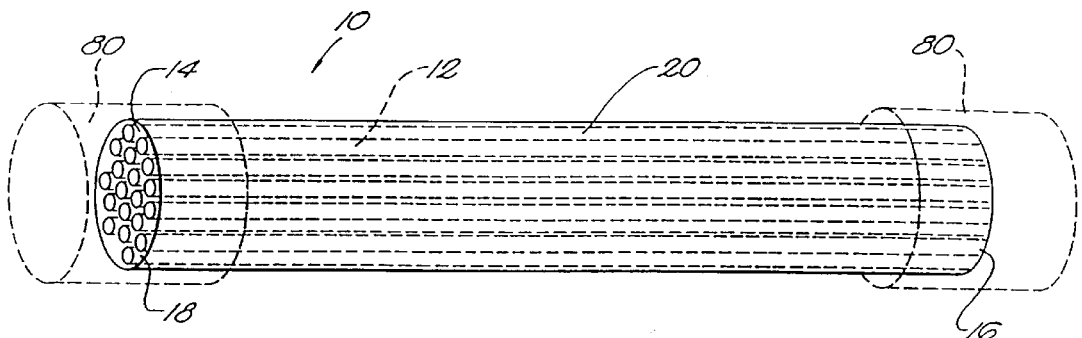
FIGS. 1 and 1A are perspective views of the nerve guidance channel of the present invention.
Figure 2:
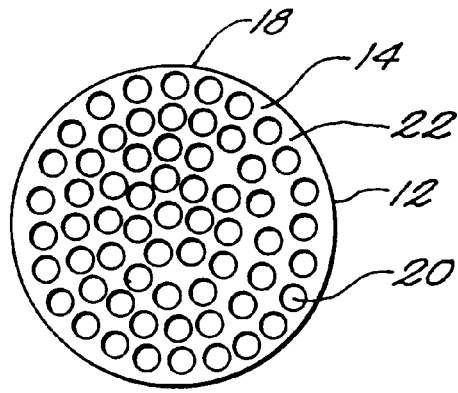
FIG. 2 is a front elevational view of the nerve guidance channel of FIG. 1, showing an end of the nerve guidance channel.

A nerve guidance channel 10 for promoting nerve regeneration is shown in FIGS. 1 and 2. The nerve guidance channel 10 includes a body 12 having a first end 14 and a second end 16.

The body 12 includes an outer shell 18 and plurality of internal lumens 20. Each of the internal lumens 20 extends continuously through the length of the body 12 to open at both the first and second ends 14, 16. The internal lumens 20 provide an internal architecture of continuous, longitudinally aligned hollow channels to promote nerve regeneration. The guidance channel can include between 5 and 5000 lumens. The number of lumens is dependent on the fascicularity of the nerve as well as the number of myelinated axons expected to regenerate. The inner diameter of each lumen can be between approximately 2–500 microns.

The walls of the internal lumens 20 can be seeded with Schwann cells, which play an important role in the regeneration of nerve tissue. The Schwann cells can be introduced to the internal lumens 20 through a dynamic seeding system which includes a closed loop system maintained within an environmentally controlled incubator. The incubator maintains the fluids within the loop at physiological temperature. The loop tubing is permeable to atmospheric gases so that oxygen and carbon dioxide can diffuse into and out of the loop fluid to provide oxygen, remove waste, and maintain physiological ph. A laminin solution or other extra-cellular matrix protein solution is first pumped through the lumens 20. The laminin solution coats the surfaces of the internal lumens 20 to improve Schwann cell adherence to the lumens. A cell suspension containing Schwann cells is then pumped through the internal lumens 20 to effect seeding of the internal lumens.

Other nerve regeneration promoting substances such as fibronectin, nerve growth factor, and extracts of central nervous tissue can be provided within the internal lumens 20 or within the polymer walls of the lumens to further promote nerve regeneration.

The internal architecture of the plurality of lumens 20 within the body 12 provides increased surface area for Schwann cell adherence. This architecture thus allows the nerve guidance channel of the present invention to contain significantly more Schwann cells than conventional single lumen guidance channels. The greater number of Schwann cells within the guidance channel can provide for increased nerve regeneration.

Figure 1A:
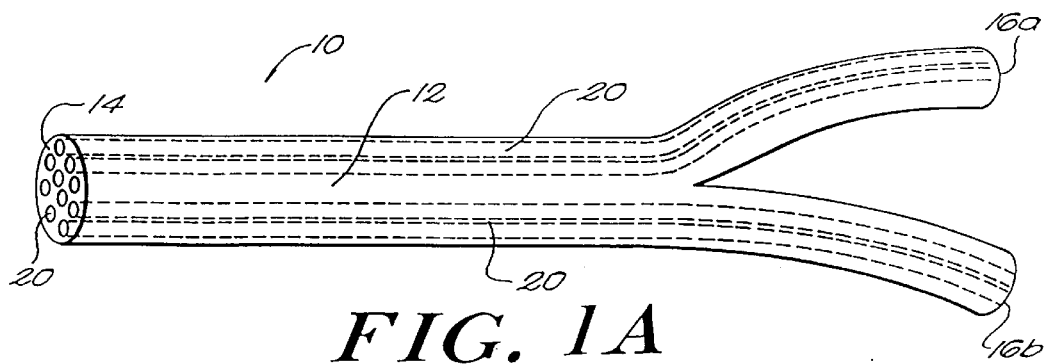

In addition, the internal architecture of lumens 20 can provide increased control over the direction of growth of different groups of regenerating nerve fibers. A single nerve can contain thousands of nerve fibers or axons. By using multiple internal lumens, each axon or a group of axons can be guided during the regenerative process through an individual internal lumen or group of lumens. Thus branching architecture can be created if desired. For example, in the simple model of a bifurcating nerve, two distinct groups of internal lumens can be provided within the body of the nerve guidance channel, as shown in FIG. 1A. At the first (proximal) end 14 of the guidance channel the two distinct groups of lumens are adjacent one another to provide a single proximal end for connection with the proximal nerve stump. At the second (distal) end 16 of the guidance channel the two distinct groups of lumens separate, so that two distinct distal ends 16a, 16b of the guidance channel are provided. Each of these ends connect to a separate branch of the distal nerve stump.

The body 12 can be constructed of a resilient, porous biocompatible material that permits fluids and nutrients to penetrate the outer surface 18 and bulk 22 of the body 12 to reach the internal lumens 20. In this manner, nutrients and oxygen are able to reach the Schwann cells and regenerative tissue present in the internal lumens. It is preferable for the pores to be sized to inhibit the growth of regenerative nerve fibers through the pores instead of along the internal lumens.

Suitable biocompatible materials for the guidance channel of the present invention include synthetic polyesters that can be arranged to form a porous structure. It is preferable for the body 12 of the nerve guidance channel to be constructed of a bioresorbable or biodegradable material so that is unnecessary to surgically remove the nerve guidance channel once nerve regeneration is complete. One skilled in the art will recognize that the rate of degradation of the material within the body can be controlled by adjusting the composition of the bioresorbable/biodegradable material. Example of suitable bioresorbable or biodegradable materials include poly-L-lactic acids, poly-lactic-coglycolic acid polymers, and polycaprolactones. Further suitable biodegradable or bioresorbable materials are described in U.S. Pat. Nos. 4,806,621; 5,399,665 and 5,654,381, each of which is incorporated herein by reference.

Figure 3:
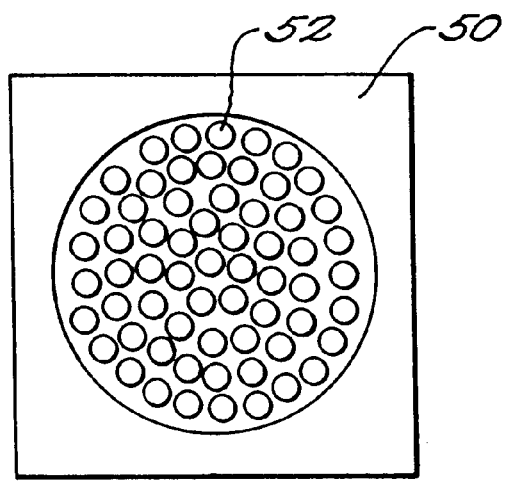
FIG. 3 is a front elevational view of a die suitable for use in constructing the nerve guidance channel of the present invention.

The nerve guidance channel of the present invention can be formed through an extrusion process in which a polymer is extruded through a die, as described in U.S. Pat. No. 5,370,681, incorporated herein by reference. The die 50 can include a plurality finger-like projections 52 for forming the internal lumens 20, as shown in FIG. 3A. Each finger-like projection 52 corresponds to an internal lumen. By varying the number of projections in the die, the number of internal lumens 20 within the body 12 can be adjusted.

Once the polymer is extruded, it is stretched and/or expanded and then sintered while being held in the stretched and/or expanded state. Stretching refers to elongation of formed polymer while expansion refers to enlargement of the formed polymer perpendicularly to its longitudinal axis. The rate of stretching and the stretch ratio, as well as the temperature, can be adjusted to produce the desired porosity of the material.

Typically, the body 12 is tubular or cylindrical in construction having a circular cross-section as shown in FIG. 2. It can however be adapted to other profiles for different applications. For example, the body can be extruded in a D-shaped with a flat or flattened surface.

Figure 4:
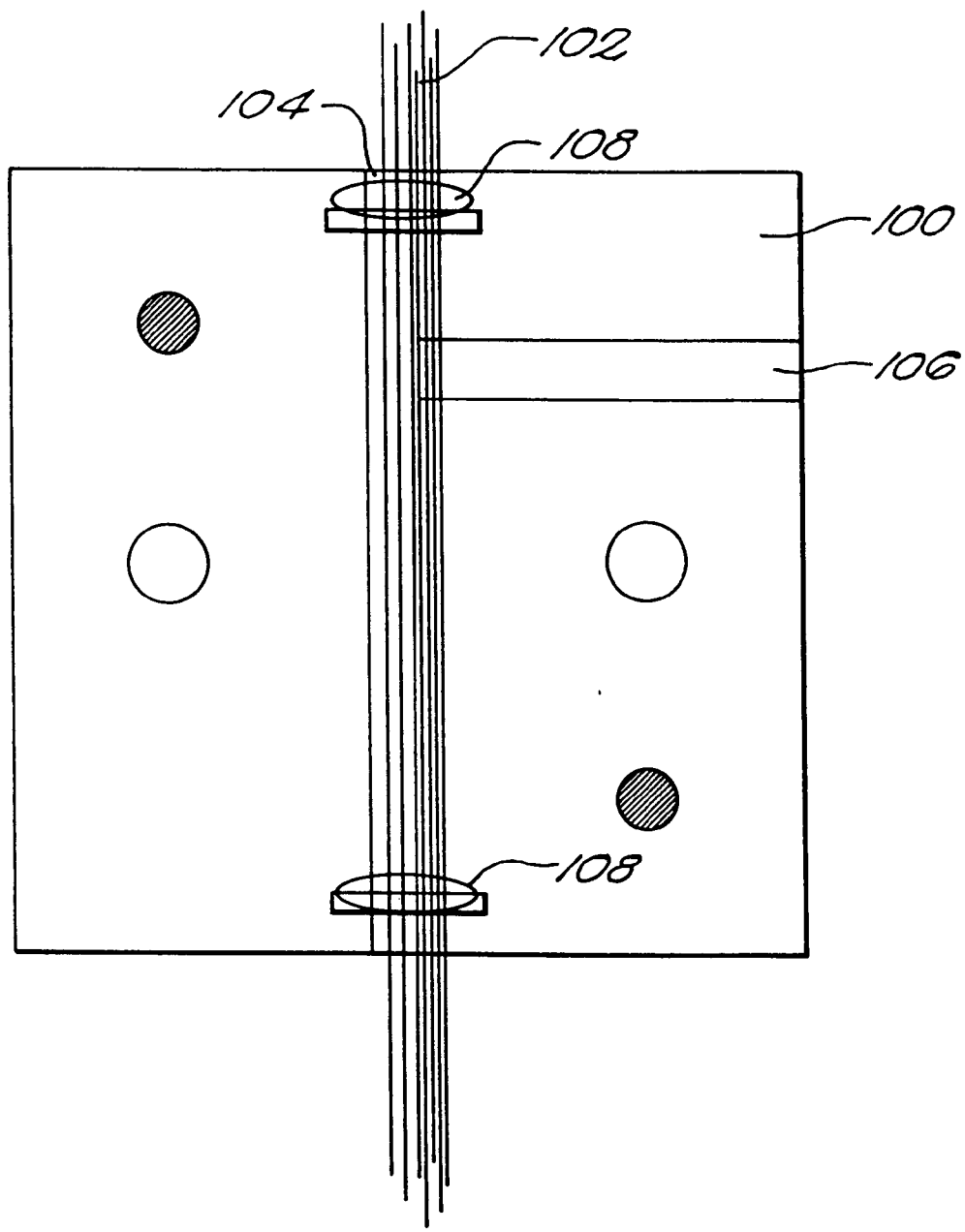
FIG. 4 is a top elevational schematic view of a mold suitable for use in constructing the nerve guidance channel of the present invention.

An alternate method of manufacturing a multi-lumen nerve guidance channel in accordance with present invention can include injection molding a polymer solution into a mold. A polymer solution, preferably including a biodegradable polymer as discussed above, and a solvent such as acetic acid, is injected through injection port 106 into mold 100 under low pressure to form the body of the nerve guidance channel, as shown in FIG. 4. The mold 100 includes a plurality of wires 102 for forming the plurality of internal lumens within the body. The internal diameter of each of the lumens 20 can be controlled within a high tolerance using wires of varying outer diameters. The wires 102 are supported by two screen disks 108 within a cylindrical cavity 104 formed in the mold 100. The polymer solution is solidified by freezing. After solidification, the polymer solution is dried by sublimation to form a plurality pores within the body.

The concentration of the solvent within the polymer solution, the rate of solidification, the polymer solution temperature, and the mold temperature can be varied to control the size and number of pores. A drug can also be dispersed throughout the solution so that it will be released into the lumens of the nerve guidance channel over time.

The nerve guidance channel 10 of the present invention is used to span the gap between proximal and distal nerve stumps. The proximal and distal nerve stumps are each connected to an end 14, 16 of the body 12. The connections can be made by suturing each of ends of the 14, 16 of the body 12 to a respective one of the proximal nerve stump and the distal nerve stump.

Alternatively, an intermediate cylindrical tube, such as suture collar 80, can be sutured to each one of the proximal and distal nerve stumps for receiving a respective one of the ends 14, 16 of the body 12. Each of the intermediate cylindrical tubes 80 includes a single lumen having an inner diameter greater than the outer diameter of the body 12. Preferably, the length of each of the intermediate cylindrical tubes is shorter than the length of the length of the body 12. Once each intermediate cylindrical tube 80 is sutured to a nerve stump, each end 14, 16 is inserted into one the intermediate cylindrical tubes to thereby connect the body 12 to each of the nerve stumps.

A further alternative means of connecting the nerve guidance channel 10 to each of the proximal and distal nerve stumps by wrapping the nerve guidance channel in a collagen sheath. The ends of the collagen sheath, which extend beyond the ends 14, 16 of the body 12, are suitable for suturing to the nerve stumps.

The nerve guidance channel and method of the present invention are not limited solely to the repair of injured or severed peripheral nerves. The guidance channel can also can be used to promote nerve regeneration in the spinal cord as well as other areas of the central nervous system such as the optic nerve.

It is to be understood that the present invention is not limited to the embodiments described above, but encompasses any and all embodiments within the scope of the following claims:

What is claimed is:

1. A guidance channel for promoting nerve regeneration comprising:

a body constructed of a biocompatible, bioresorbable, polymeric material and having a first end for connection to a proximal stump of a severed nerve and a second end for connection to a distal stump of the severed nerve, the body including a plurality of internal lumens extending between the first and second end to facilitate rejoining of the proximal and distal stumps of the severed nerve.

2. The guidance channel according to claim 1, wherein the plurality of lumens comprises approximately 5–5000 lumens.

3. The guidance channel according to claim 1, wherein the inner diameter of each lumen of the plurality of lumens is approximately 2–500 microns.

4. The guidance channel according to claim 1, further comprising Schwann cells incorporated within at least one of the lumens of the plurality of lumens.

5. The guidance channel according to claim 4, wherein the Schwann cells adhere to the interior surfaces of the lumens of the plurality of lumens.

6. The guidance channel according to claim 1, wherein the body comprises a tubular configuration.

7. The nerve guidance channel according to claim 1, wherein the body comprises a porous membrane structure containing a plurality of pores for permitting nutrients and oxygen to pass through the body to reach the lumens.

8. The nerve guidance channel according to claim 7, wherein the pores are sized to inhibit nerve regeneration through the pores.

9. A method of promoting nerve regeneration between the severed stumps of a nerve, the method comprising the steps of:

providing a nerve guidance channel constructed of a biocompatible polymeric material and having first and second ends, the guidance channel including a plurality of internal lumens, connecting the proximal stump of the nerve to the first end of the guidance channel, and connecting the distal stump of the nerve to the second end of the guidance channel whereby nerve regeneration occurs within the plurality of internal lumens of the guidance channel between the severed stumps of the nerves.

10. The method according to claim 9, further comprising the step of seeding the lumens of the plurality of internal lumens with Schwann cells.

11. A method of manufacturing a multi-lumen nerve guidance channel, the method comprising the steps of:

preparing a polymer solution comprising a polymer and a solvent, injecting the polymer solution into a mold to form the body of the nerve guidance channel, the mold including a plurality of wires for forming a plurality of internal lumens within the body, solidifying the polymer solution by freezing the body, and drying the body by sublimation to form a plurality of pores within the body.

12. The method of claim 11, wherein the polymer comprises a bioresorbable material.

13. The method of claim 11, further comprising the step of adjusting the concentration of the solvent within the polymer solution to control the size and number of pores formed within the body.

14. The method according to claim 11, further comprising the step of seeding the internal lumens with Schwann cells.

* * * * *